(12) United States Patent　　　　(10) Patent No.: US 12,588,858 B2

Govari　　　　　　　　　　　　　　(45) Date of Patent: Mar. 31, 2026

(54) WEIGHTING PROJECTED ELECTROPHYSIOLOGICAL WAVE VELOCITY WITH SIGMOID CURVE

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 204 days.

(21) Appl. No.: 17/467,566

(22) Filed: Sep. 7, 2021

(65) Prior Publication Data

US 2023/0075595 A1　　Mar. 9, 2023

(51) Int. Cl.
A61B 5/287　　　(2021.01)
A61B 5/341　　　(2021.01)
A61B 5/367　　　(2021.01)

(52) U.S. Cl.
CPC .............. A61B 5/367 (2021.01); A61B 5/287 (2021.01); A61B 5/341 (2021.01)

(58) Field of Classification Search
CPC .......... A61B 5/367; A61B 5/341; A61B 5/287
USPC ........................................................ 600/512
See application file for complete search history.

(56) References Cited

U.S. PATENT DOCUMENTS

| | | | |
|---|---|---|---|
| 5,706,402 A * | 1/1998 | Bell | G06N 3/088 706/22 |
| 6,301,496 B1 | 10/2001 | Reisfeld | |
| 7,158,686 B2 | 1/2007 | Gindele | |
| 8,478,072 B2 | 7/2013 | Aisaka et al. | |
| 9,918,649 B2 | 3/2018 | Thakur et al. | |
| 2013/0342758 A1 | 12/2013 | Greisen et al. | |
| 2014/0200874 A1* | 7/2014 | Zeng | A61B 5/339 703/11 |
| 2016/0143696 A1* | 5/2016 | Govari | A61B 18/1206 606/41 |
| 2017/0049348 A1 | 2/2017 | Deno et al. | |
| 2018/0325400 A1* | 11/2018 | Dubois | A61B 18/1492 |

FOREIGN PATENT DOCUMENTS

| | | | |
|---|---|---|---|
| EP | 1070480 A2 | 1/2001 | |
| WO | WO-03003905 A2 * | 1/2003 | A61B 5/044 |

OTHER PUBLICATIONS

Extended European Search Report and Search Opinion dated Jan. 30, 2023, from corresponding European Application No. 22194162. 8.

* cited by examiner

*Primary Examiner* — Nicole F Johnson

(57) ABSTRACT

A method includes receiving, for at least a region of an anatomical map of at least a portion of a heart, positions and respective electrophysiological (EP) wave propagation velocity vectors, the vectors having respective magnitudes. The magnitudes are nonlinearly scaled. Scaled vectors having the scaled magnitudes, are presented by being overlaid on the anatomical map.

12 Claims, 2 Drawing Sheets

DISPLAYED
VECTOR LENGTH
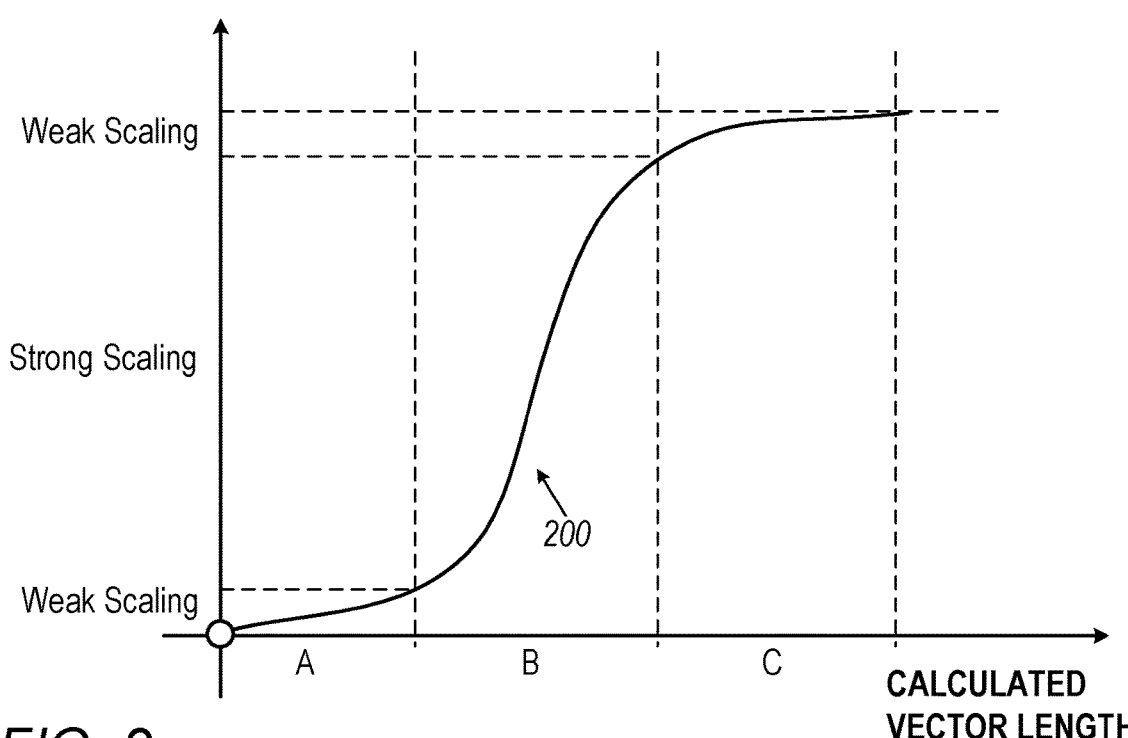
*FIG. 2*
*FIG. 3*
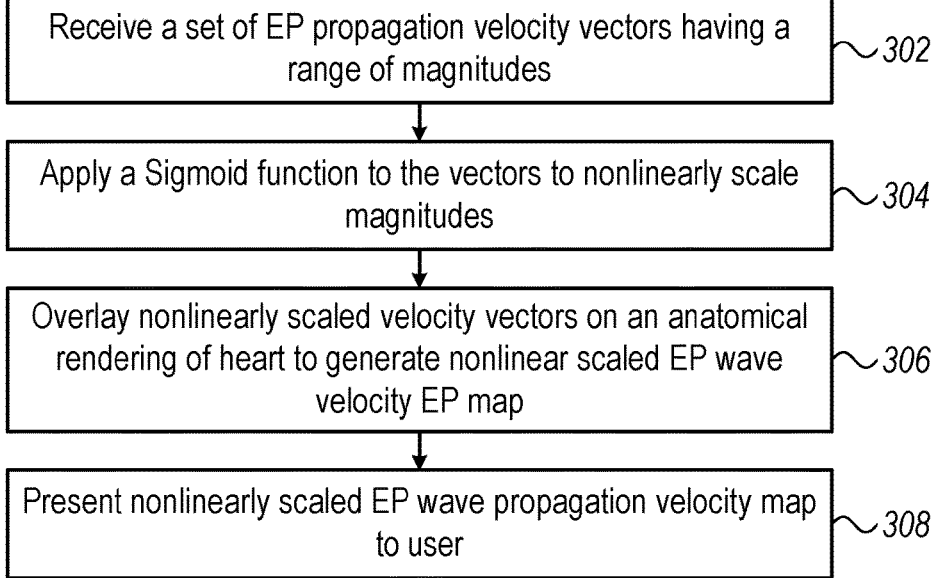

WEIGHTING PROJECTED ELECTROPHYSIOLOGICAL WAVE VELOCITY WITH SIGMOID CURVE

FIELD OF THE INVENTION

The present invention relates generally to electrophysiological mapping, and particularly to visualization of cardiac electrophysiological maps.

BACKGROUND OF THE INVENTION

Visualization methods of a cardiac electrophysiological (EP) map, to ease an interpretation of the EP map, were previously proposed in the patent literature. For example, U.S. Patent Application Publication 2017/0049348 describes a method for determining EP properties of cardiac tissue in order classify an arrhythmia. An eccentricity parameter reflecting the uniformity of a local conduction velocity, and divergence and curl-like sums or closed path integral parameters associated with the local velocity vectors are provided, and a rhythm classification responsive to catheter movement is displayed, thereby facilitating identification of types and causes of arrhythmia disorders. In an embodiment, conduction velocity vector maps are coupled with local activation time (LAT) maps.

As another example, U.S. Pat. No. 6,301,496 describes a method of diagnosing an abnormal condition in a biological structure, such as the heart, including the steps of measuring a physiological response in at least three sampled points on a surface of the biological structure, calculating a vector function related to the response, displaying a representation of the vector function, and inferring the abnormal condition from the representation. The method is deemed therein as useful for diagnosing cardiac arrhythmias, in which case the physiological response is a voltage, from which is inferred a local activation time and the vector function is a gradient of the local activation time, specifically, a conduction velocity.

SUMMARY OF THE INVENTION

An embodiment of the present invention that is described hereinafter provides a method including receiving, for at least a region of an anatomical map of at least a portion of a heart, positions and respective electrophysiological (EP) wave propagation velocity vectors, the vectors having respective magnitudes. The magnitudes are nonlinearly scaled. Scaled vectors having the scaled magnitudes, are presented by being overlaid on the anatomical map.

In some embodiments, nonlinearly scaling the magnitudes includes dividing a range of the magnitudes into a low-magnitude region, a high-magnitude region, and an intermediate-magnitude region between the low-magnitude region and the high-magnitude region. Magnitude differences within the intermediate-magnitude region are emphasized relative to the low-magnitude region and the high-magnitude region.

In some embodiments, nonlinearly scaling the magnitudes includes applying a sigmoid function to the magnitudes.

In other embodiments, presenting the scaled vectors includes visualizing the scaled vectors as arrows.

There is additionally provided, in accordance with another embodiment of the present invention, a system including an interface and a processor. The interface is configured to receive, for at least a region of an anatomical map of at least a portion of a heart, positions and respective electrophysiological (EP) wave propagation velocity vectors, the vectors having respective magnitudes. The processor is configured to nonlinearly scale the magnitudes, and to present scaled vectors, having the scaled magnitudes, overlaid on the anatomical map.

The present invention will be more fully understood from the following detailed description of the embodiments thereof, taken together with the drawings in which:

BRIEF DESCRIPTION OF THE DRAWINGS

FIG. 2 is a graph of a sigmoid function used by the processor of the mapping system of FIG. 1 to generate the EP map shown in FIG. 1, in accordance with an embodiment of the present invention; and FIG. 3 is flow chart that schematically illustrates a method and algorithm for nonlinearly scaling wave propagation presented in an EP map using the sigmoid function of FIG. 2, in accordance with an embodiment of the present invention.

DETAILED DESCRIPTION OF EMBODIMENTS

Overview

Figure 1:
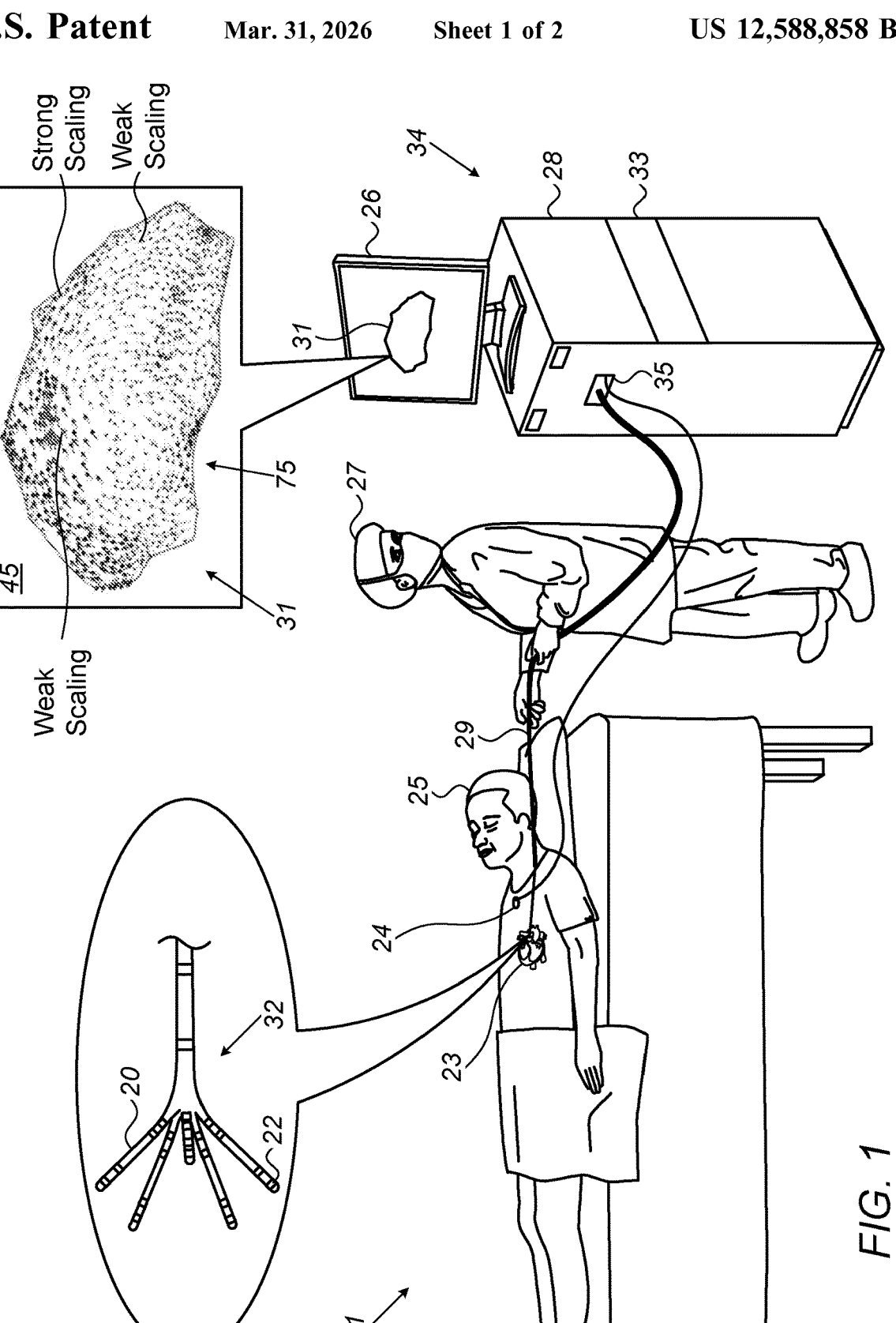
FIG. 1 is a schematic, pictorial illustration of a cardiac three-dimensional (3D) navigation and electrophysiological (EP) mapping system, in accordance with an embodiment of the present invention.

In order to characterize cardiac electrophysiological (EP) abnormalities of a patient, a catheter-based EP mapping system may be used for generating an EP map of least part of the heart of the patient, such as an EP map of a cardiac chamber. In a typical catheter-based EP mapping procedure, a distal end of a catheter, which comprises one or more sensing electrodes, is inserted into the heart to sense EP signals. As a physician operating the system moves the distal end inside the heart, the EP mapping system acquires EP signals at various cardiac locations, as well as the respective positions of the distal end. Based on these acquired signals, a processor of the mapping system generates the required EP map.

Typically, the processor of the EP mapping system presents the measured EP map, for example a map of EP wavefront propagation, overlaid (e.g., projected) on a heart anatomy visualized by, for example, a volume (3D) rendering of at least a portion of the heart. Such an overlaid rendering may be very useful in diagnosing cardiac irregularities. For example, the processor may overlay EP wavefront velocity vectors on an anatomical map, where the magnitude and direction of the vectors give a measure of the cardiac electrical activity. An aggregate of such vectors may indicate a clinical pattern, such as an anomalous conduction path causing an arrhythmia (e.g., a rotor).

Various methods can be used for calculating the velocity of the wave velocity in the heart, and the velocity may be displayed as described above. However, a surgeon observing the velocities is not typically interested in value differences of the velocities at their extremities, i.e., when the velocities are very low or very high. Typically, the surgeon is mostly interested in differences in values in an intermediate range of velocities.

Embodiments of the present invention that are described hereinafter use a non-uniform scaling function (e.g., a non-linear scaling function) to suppress changes in the low and high velocities and at least retain or emphasize changes in the intermediate range of velocities. In particular, the disclosed technique applies a processor to put a low weighting on the very high values (magnitude of the velocity vector) and on the very low values, because these value ranges are suspected of containing outliers due to errors or noise. High weighting may be applied on the intermediate range, because the intermediate range is expected to be more representative of the actual velocity of the propagation wave.

To this end, a processor applies a nonlinear scaling function to the magnitudes of the EP wavefront propagation vectors, to redraw the EP wavefront propagation. The scaled vectors are accordingly overlaid on a heart anatomy. A user may look at the original EP map and/or at the nonlinearly scaled map.

Examples of a nonlinear scaling function that can be used include a sigmoid function, a suitable polynomial function and a piecewise linear function, to name only a few.

Typically, the processor is programmed in software containing a particular algorithm that enables the processor to conduct each of the processor-related steps and functions outlined above.

The disclosed visualization technique to nonlinearly scale EP wavefront propagation on 3D cardiac anatomy may improve the diagnostic value of catheter-based EP mapping procedures.

System Description

FIG. 1 is a schematic, pictorial illustration of a cardiac three-dimensional (3D) navigation and electrophysiological (EP) mapping system 21, in accordance with an embodiment of the present invention. System 21 may be configured to analyze substantially any physiological parameter or combinations of such parameters. In the description herein, by way of example, EP signals analyzed are assumed to be potential-spatiotemporal relationships of intra-cardiac electrograms (EGM) and/or extra-cardiac (body surface) electrocardiograms (ECG). In order to fully characterize such relationships, a processor 28 uses the ECG signals to produce one or more EP maps, such as a local activation time (LAT) map and/or an EP wave vector map 31.

FIG. 1 shows an investigative procedure wherein system 21 measures actual electrical activity of a heart 23 using a probe 29. Typically, probe 29 comprises a catheter which is inserted into the body of patient 25 during an EP mapping procedure performed by a physician 27 using system 21. A distal end assembly 32 of probe 29 is assumed to have multiple electrodes 22. In the shown embodiment, distal end assembly 32 is multi-arm type (with five arms 20), though the distal end may have any other shape, such as a basket or a loop.

The measured EP signals are inputted to processor 28 via interface circuits 35, and, as noted above and among other usages, are used to create EP wave velocity map 31, presented on a display 26, of at least part of the wall tissue of heart 23 of a patient 25. In general, display 26, which typically presents a graphic user interface to the physician, provides a visual representation of the EP signals sensed by electrodes 22, and/or an image and/or map 31 of heart 23 while it is being investigated.

System 21 is controlled by a system processor 28 in communication with a memory 33. In some embodiments, processor 28 uses memory 33 for storing EP wave velocity map 31 of at least part of wall tissue of heart 23 of patient 25. Processor 28 is typically mounted in a console 34.

As seen in an inset 45, EP wave vector map 31 comprises a plurality of velocity vectors 75 (not all labeled for the sake of simplicity) describing the propagation velocity of activation wavefronts associated with, for example, the activation times. Each vector 75 is visualized as an arrow that is overlaid at a respective position of map and has a respective magnitude and a respective direction. The magnitude of the arrow is indicative of (although not necessarily proportional to, as will be explained below) the magnitude of the EP wave at the respective position. The direction of the arrow is indicative of the direction of the EP wave at the respective position.

In particular, as seen in inset 45, EP wave vector map 31 comprises a plurality of velocity vectors 75 that utilize the aforementioned non-uniform scaling function (e.g., sigmoid function) to emphasize magnitude differences in a selected range of vector magnitudes that is of interest. Non-uniform scaling described in greater detail in FIG. 2. Extreme ends of the range of velocity vector magnitudes, i.e., very small and very large vectors, as defined below, undergo weaker scaling to downplay differences that are irrelevant to a viewer of EP wave vector map 31.

In the context of this disclosure, the term "anatomical map" refers to a map that models the 3D shape of at least a portion of the heart, and may have one or more parameters overlaid thereon. An EP map is one special case of an anatomical map, with which one or more electrophysiological parameters are overlaid. An LAT map or an EP wave map is an example of an EP map, and thus also regarded as a type of anatomical map.

To produce a map such as map 31, processor 28 typically tracks the location of distal end 32 of probe 29 within heart 23 of patient 25. The processor may use any method for location tracking probes known in the art. For example, processor 28 may track probe distal end assembly 32 by measuring impedances between electrode 22 and external patch electrodes 24 attached to patient's 25 skin (only one patch electrode is shown for clarity). The Carto3® system, produced by Biosense-Webster (Irvine, California) uses such impedance measurements for location tracking.

The software run by processor 28 may be downloaded to processor 28 in electronic form, over a network, for example, or it may, alternatively or additionally, be provided and/or stored on non-transitory tangible media, such as magnetic, optical, or electronic memory. In particular, processor 28 runs a dedicated algorithm that enables processor 28 to perform the disclosed steps, as described below.

Weighting Projected EP Wave Velocity with Sigmoid Curve

FIG. 2 is a graph of a sigmoid function 200 used by the processor of mapping system 21 of FIG. 1 to generate EP map 31 shown in FIG. 1, in accordance with an embodiment of the present invention.

The graph has a horizontal axis representing the calculated wave velocity magnitudes before scaling, and a vertical axis representing the wave velocity magnitudes after scaling (the magnitudes of vectors 75 that are displayed to the user). The range of magnitudes before scaling is divided into three regions: A for low velocities, B for intermediate velocities, and C for high velocities. Applying sigmoid curve 200 to the calculated magnitudes yields small changes in the displayed values in region A and region C, (i.e., weak scaling). However, in region B, which corresponds to intermediate velocity values, changes in magnitude are emphasized (i.e., undergo strong scaling) in the displayed value.

FIG. 2 is brought by way of example. While FIG. 2 shows a sigmoid function, any other suitable nonlinear function may be used, such as a polynomial or piecewise linear function.

FIG. 3 is flow chart that schematically illustrates a method and algorithm for nonlinearly scaling wave propagation presented in EP map 31 using the sigmoid function 200 of FIG. 2, in accordance with an embodiment of the present invention.

The algorithm, according to the presented embodiment, carries out a process that begins with processor 28 receiving a set of EP propagation velocity vectors having a range of magnitudes, at an EP mapping data receiving step 302.

Next, at nonlinear scaling step 304, processor 28 applies a nonlinear scaling function (e.g., a sigmoid function) over the range to the vectors, to nonlinearly scale the vectors as described in FIG. 2.

Next, processor 28 overlays the nonlinearly scaled EP velocity vectors on an anatomical rendering of a heart to obtain an EP map such as EP map 31 of FIG. 1, at a scaled EP map generation step 306. Processor 28 presents the resulting visualization (nonlinearly scaled EP wave velocities) to physician 27 on display 26.

The example flow chart shown in FIG. 3 is chosen purely for the sake of conceptual clarity. The present embodiment also comprises additional steps of the algorithm. Examples include additional visualizations. Such additional steps have been omitted from the disclosure herein purposely on order to provide a more simplified flow chart.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:

receiving by an interface, for at least a region of an anatomical map of at least a portion of a heart, electrophysiological signals from a probe comprising a distal end assembly including a plurality of electrodes configured to detect electrophysiological activity in the heart and output the electrophysiological signals;

calculating, with one or more processors, positions and respective electrophysiological wave propagation velocity vectors based at least in part on the electrophysiological signals, the electrophysiological wave propagation velocity vectors having respective magnitudes and directions;

nonlinearly scaling the magnitudes via the one or more processors, by:

dividing a range of the magnitudes into a low-magnitude value region, a high-magnitude value region, and an intermediate-magnitude value region, the low-magnitude value region including magnitudes less than or equal to a first threshold, the high-magnitude region including magnitudes greater than or equal to a second threshold, and the intermediate-magnitude value region including magnitudes between the first threshold and the second threshold, scaling magnitudes in the low-magnitude value region to a first weight, scaling magnitudes in the intermediate-magnitude value region to a second weight, and scaling magnitudes within the high-magnitude value region to a third weight, the second weight being greater than the first weight and the third weight;

outputting, via the one or more processors, scaled electrophysiological wave propagation velocity vectors for display to a user, the scaled electrophysiological wave propagation velocity vectors being represented by arrows on a display, each arrow being overlaid on the anatomical map; and causing at least one of:

visual emphasis via the display of magnitude differences within the intermediate-magnitude region relative to the low-magnitude region and the high-magnitude region; and visual suppression via the display of magnitude differences within the low-magnitude region and the high-magnitude region relative to the intermediate-magnitude region by causing lengths of the respective arrows as displayed to be adjusted so as to indicate the scaled magnitude of the corresponding electrophysiological wave propagation velocity vectors.

2. The method according to claim 1, wherein nonlinearly scaling the magnitudes comprises applying a sigmoid function to the magnitudes for scaling the magnitudes in each of the low-, intermediate- and high-magnitude value regions.

3. The method according to claim 1, wherein a direction of each arrow is indicative of a direction of the corresponding electrophysiological wave propagation vector.

4. The method according to claim 2, wherein a first inflection point of the sigmoid function is provided at the first threshold, and a second inflection point of the sigmoid function is provided at the second threshold.

5. The method according to claim 1, wherein the method is a method for detection of a clinical pattern.

6. The method according to claim 1, wherein the electrophysiological signals are received, and the display is output with the arrows during an investigative procedure.

7. A system, comprising:

a probe comprising a plurality of electrodes configured to be inserted into a heart of a patient, detect electrophysiological activity in the heart, and output electrophysiological signals;

an interface which is configured to receive the electrophysiological signals from the probe;

one or more processors, which are configured to:

calculate at least positions and respective electrophysiological wave propagation velocity vectors based at least in part on the electrophysiological signals relative to an anatomical map of at least a portion of the heart, the electrophysiological wave propagation velocity vectors having respective magnitudes and directions;

nonlinearly scale the magnitudes by:

dividing a range of the magnitudes into a low-magnitude value region, a high-magnitude value region, and an intermediate-magnitude value region, the low-magnitude value region including magnitudes less than or equal to a first threshold, the high-magnitude region including magnitudes greater than or equal to a second threshold, and the intermediate-magnitude value region including magnitudes between the first threshold and the second threshold, scaling magnitudes in the low-magnitude value region to a first weight, scaling magnitudes in the intermediate-magnitude value region to a second weight, and scaling magnitudes within the high-magnitude value region to a third weight, the second weight being greater than the first weight and the third weight; and calculate lengths of arrows representing the respective electrophysiological wave propagation velocity vectors, the length of each arrow being adjusted to indicate the scaled magnitude of the corresponding electrophysiological wave propagation velocity vectors; and a display configured to present to a user the arrows overlaid on at least a region of the anatomical map, each arrow having a respective length that is adjusted to be indicative of a corresponding scaled magnitude, the lengths of the respective arrows at least one of:

visually emphasizing magnitude differences within the intermediate-magnitude region relative to the low-magnitude region and the high-magnitude region, and visually suppressing magnitude differences within the low-magnitude region and the high-magnitude region relative to the intermediate-magnitude region.

8. The system according to claim 7, wherein the one or more processors are configured to nonlinearly scale the magnitudes by applying a sigmoid function to the magnitudes for scaling the magnitudes in each of the low-, intermediate- and high-magnitude value regions.

9. The system according to claim 7, wherein a direction of each arrow is indicative of a direction of the corresponding electrophysiological wave propagation vector.

10. The system according to claim 8, wherein a first inflection point of the sigmoid function is provided at the first threshold, and a second inflection point of the sigmoid function is provided at the second threshold.

11. The system according to claim 7, wherein the system is a system for detection of a clinical pattern.

12. The system according to claim 7, wherein the electrophysiological signals are received, and the display is output with the arrows during an investigative procedure.

* * * * *